(12) United States Patent
Yasui et al.

(10) Patent No.: US 12,038,360 B2
(45) Date of Patent: Jul. 16, 2024

(54) DEVICE TO BE USED FOR CAPTURING EXTRACELLULAR VESICLES, AND PRESERVATION METHOD AND TRANSPORT METHOD FOR EXTRACELLULAR VESICLES

(71) Applicant: CRAIF INC., Tokyo (JP)

(72) Inventors: Takao Yasui, Nagoya (JP); Yoshinobu Baba, Nagoya (JP); Hirotaka Koga, Osaka (JP)

(73) Assignee: CRAIF INC., Tokyo (JP)

( * ) Notice: Subject to any disclaimer, the term of this patent is extended or adjusted under 35 U.S.C. 154(b) by 602 days.

(21) Appl. No.: 17/289,282

(22) PCT Filed: Oct. 30, 2019

(86) PCT No.: PCT/JP2019/042498
§ 371 (c)(1),
(2) Date: Sep. 27, 2021

(87) PCT Pub. No.: WO2020/090859
PCT Pub. Date: May 7, 2020

(65) Prior Publication Data
US 2022/0026323 A1   Jan. 27, 2022

(30) Foreign Application Priority Data

Oct. 30, 2018 (JP) .................................. 2018-203526
Feb. 28, 2019 (JP) .................................. 2019-036490

(51) Int. Cl.
*G01N 1/40* (2006.01)
*B82Y 5/00* (2011.01)
(Continued)

(52) U.S. Cl.
CPC ....... *G01N 1/4077* (2013.01); *C12N 15/1006* (2013.01); *D04H 1/425* (2013.01);
(Continued)

(58) Field of Classification Search
None
See application file for complete search history.

(56) References Cited

U.S. PATENT DOCUMENTS

| 2012/0045487 A1 | 2/2012 | Lahann et al. |
| 2014/0030805 A1 | 1/2014 | Kasuto et al. |

(Continued)

FOREIGN PATENT DOCUMENTS

| CN | 108633877 A | 10/2018 |
| WO | 2014/034146 A1 | 3/2014 |
| WO | 2017/154951 A1 | 9/2017 |

OTHER PUBLICATIONS

Novel label-free method for extracellular-vesicle enrichment from biological fluids and cell culture medium. Prateek Singh; Jonne Ukkola; Sry D. Hujaya. ISEV 2018 abstract book. Apr. 30, 2018 (Year: 2018).*

(Continued)

*Primary Examiner* — Kristina M Deherrera
*Assistant Examiner* — Mark A Shabman
(74) *Attorney, Agent, or Firm* — McBee Moore & Vanik IP, LLC

(57) ABSTRACT

The present invention provides a novel miRNA extraction method and a method for analyzing miRNA extracted by using said miRNA extraction method. According to the present invention, provided is, for example, a method for extracting miRNA from extracellular vesicles in a sample solution, by using a device capable of capturing extracellular vesicles, the miRNA extraction method comprising: an extracellular vesicle capturing step for capturing extracellular vesicles in a sample solution onto a device by bringing the sample solution and the device in contact with each other; and a miRNA extraction step for homogenizing the extracellular vesicles by bringing the device having captured the extracellular vesicles in contact with a homogenization (Continued)

A

B

C

D liquid for extracellular vesicles to extract miRNA from the extracellular vesicle into the homogenization liquid.

14 Claims, 11 Drawing Sheets

(51) Int. Cl.
*B82Y 35/00* (2011.01)
*B82Y 40/00* (2011.01)
*C12N 15/10* (2006.01)
*D04H 1/425* (2012.01)

(52) U.S. Cl.
CPC .............. *B82Y 5/00* (2013.01); *B82Y 35/00* (2013.01); *B82Y 40/00* (2013.01); *D10B 2201/01* (2013.01); *G01N 2001/4088* (2013.01)

(56) References Cited

U.S. PATENT DOCUMENTS

| | | | | |
|---|---|---|---|---|
| 2014/0113295 | A1* | 4/2014 | Park | C12P 19/34 435/6.12 |
| 2015/0148258 | A1 | 5/2015 | Martinez et al. | |
| 2015/0260710 | A1* | 9/2015 | Tseng | G01N 33/54346 506/13 |
| 2015/0283543 | A1 | 10/2015 | Mckean | |
| 2015/0285808 | A1* | 10/2015 | Nagrath | G01N 33/54366 435/7.23 |
| 2015/0353920 | A1* | 12/2015 | Enderle | C12N 15/1006 536/25.41 |
| 2017/0198280 | A1* | 7/2017 | Skog | C12N 15/1006 |
| 2018/0266951 | A1* | 9/2018 | Spero | G01N 21/631 |

OTHER PUBLICATIONS

Review: Isolation and Detection of Tumor-Derived Extracellular Vesicles Parissa Ziaei, Clifford E. Berkman, and M. Grant Norton. ACS Applied Nano Materials 2018 1 (5), 2004-2020 (Year: 2018).*

Stretchable and Strong Cellulose Nanopaper Structures Based on Polymer-Coated Nanofiber Networks: An Alternative to Nonwoven Porous Membranes from Electrospinning. Houssine Sehaqui, Seira Morimune, Takashi Nishino, and Lars A. Berglund Biomacromolecules 2012 13 (11), 3661-3667 (Year: 2012).*

Prateek Singh et al., "Novel label-free method for extracellular-vesicle enrichment from biological fluids and cell culture medium", Journal of Extracellular Vesicles, May 15, 2018, p. 223, vol. 7, PS04.14.

Proteomics and Precision Medicine, Shangai Jiao Tong University press, 2017, p. 222, English abstract.

International Search Report of International Patent Application No. PCT/JP2019/042498 dated Jan. 28, 2020.

Yasui et al., "Identifying "cancer" from urinary microRNA" Non-official translation, Nagoya University Joint Press Release, Dec. 16, 2017, https://www.jst.go.jp/pr/announce/20171216/index.html.

Yasui et al., "Unveiling massive numbers of cancer-related urinary-microRNA candidates via nanowires", Science Advances, Dec. 15, 2017, vol. 3 No. 12, e1701133.

Melo, Sonia et. al, "Cancer Exosomes Perform Cell-Independent MicroRNA Biogenesis and Promote Tumorigenesis", Cancer Cell, Nov. 1, 2014, pp. 707-721, vol. 26.

Michael, Amanda et. al, "Exosomes from Human Saliva as a Source of microRNA Biomarkers", Oral Dis., 2010, pp. 34-38, vol. 16, No. 1.

Iwai, Kazuya et. al, "Isolation of human salivary extracellular vesicles by iodixanol density gradient ultracentrifugation and their characterizations", Journal of Extracellular Vesicles, 2016, vol. 5:30829.

Nagoya University et al., "Identifying "cancer" from microRNA in urine", Press Release of Japan Science and Technology Agency, 2017 (machine translation attached).

Nagoya University, Kyushu University, National Cancer Center, Japan Science and Technology Agency (JST) Japanese Medical Research and Development Agency (AME), the National Research and Development Agency, Japan Science and Technology Agency Press Release, Dec. 16, 2017 ; Japan, Dec. 16, 2017; https://www.jst.go.jp/pr/announce/20171216/index.html , specifying "cancer," in the National Research and Development Agency, Japan [English translation of https://www.jst.go.jp/pr/announce/20171216/index.html included].

* cited by examiner

1,1b

DEVICE TO BE USED FOR CAPTURING EXTRACELLULAR VESICLES, AND PRESERVATION METHOD AND TRANSPORT METHOD FOR EXTRACELLULAR VESICLES

CROSS-REFERENCE TO RELATED APPLICATIONS

This application is the National Stage entry of International Application No. PCT/JP2019/042498, filed 30 Oct. 2019, which claims priority to Japanese Application No. 2018-203526, filed 30 Oct. 2018.

BACKGROUND

Technical Field

The disclosure in this application relates to devices to be used for capturing extracellular vesicles (Extracellular Vesicles, exosomes; hereinafter sometimes referred to as "EVs") contained in a sample, methods of preserving and transferring extracellular vesicles.

Description of Related Art

EVs are membrane endoplasmic reticula of about 40 nm-1000 nm in size secreted by cells in vivo and are present in body fluids such as blood, urine, saliva, and semen. Membrane proteins, adhesion molecules, enzymes, and the like derived from secretory cells are present on the surfaces, and nucleic acids such as mRNA and miRNA are contained inside. Therefore, they propagate to other cells and are taken up, thus affecting the recipient cells.

In recent years, it has become clear that EVs induce cancer metastasis as one of their functions in vivo, and this has attracted attention. Cancer metastasis refers to the propagation of cancer cells from the site of cancer to other organs via blood vessels and lymph and the growth, and the high mortality from cancer is also attributable to this metastasis. Regarding the development of this cancer metastasis, researches on EVs and cancer metastasis have been reported, including EVs from cancer cells of the cancer primary lesion propagating through blood vessels to other organs, forming a cancer metastatic niche, and EVs derived from cancer cells inducing abnormal proliferation of normal cells and developing into cancer tumorigenesis (see Non-Patent Literature 1).

It is also known that miRNA contained in EVs is used as a biomarker for diseases [Non-Patent Literatures 2 and 3].

CITATION LIST

Non-Patent Literatures

Non-Patent Literature 1: Sonia A. Melo, et al., "Cancer Exosomes Perform Cell-Independent MicroRNA Biogenesis and Promote Tumorigenesis," Cancer Cell 26, 707-721, Nov. 10, 2014 http://dx.doi.org/10.1016/j.ccell.2014.09.005

Non-Patent Literature 2: Amanda Michael, et al., "Exosomes from Human Saliva as a Source of microRNA Biomarkers," Oral Dis. 2010 January; 16(1):34-38. doi: 10.1111/j.0.1601-0825.2009.01604.x.

Non-Patent Literature 3: Kazuya Iwai, et al., "Isolation of human salivary extracellular vesicles by iodixanol density gradient ultracentrifugation and their characterizations," Journal of Extracellular Vesicles 2016, 5: 30829-http://dx.doi.org/10.3402/jev.v5.30829

SUMMARY OF INVENTION

Technical Problem

As described in Non-Patent Literatures 2 and 3 described above, it is known to use miRNA contained in EVs in a sample (saliva in Non-Patent Documents 2 and 3) as a biomarker for diseases. By the way, it is described in Non-Patent Literatures 2 and 3 that EVs are collected from the sample solution by ultracentrifugation of the sample solution. However, separation by ultracentrifugation requires to collect the fractions containing EVs after the ultracentrifugation.

Therefore, there is a problem that an ultracentrifugation step is essential, and the work procedure increases. Furthermore, when the amount of the sample solution is small, in order to analyze a trace amount of miRNA contained in the sample solution, it is necessary to reduce the loss when collecting EVs contained in the sample solution. However, in methods of collecting EVs by ultracentrifugation, there is a problem that a part of EVs contained in a sample may be discarded during the operation process of collecting the fraction containing EVs. Further, as a method for separating EVs in a sample solution, an aggregation reagent method using a commercially available kit is also known in addition to the ultracentrifugal method. However, even with respect to the aggregation reagent method, after aggregating EVs in the sample solution, it is necessary to separate the aggregated EVs by centrifugation or the like. Thus, there is a problem that the work procedure increases and a loss occurs during the operation of separation of EVs. Therefore, there is a need for a device to be used for collecting EVs from a sample solution in a simple and efficient manner (hereinafter sometimes simply referred to as a "device").

The disclosure of the present application has been made to solve the above-mentioned problems, and as a result of intensive studies, it has been newly discovered that [1] EVs can be captured in a device by contacting a device with a sample solution using a device including a nanostructure body capable of capturing EVs, [2] EVs can be captured in the device by directly contacting the device with a crushing liquid of EVs, [3] miRNA can be directly extracted from EVs captured in the device without requiring a step of separating EVs captured in the device. It was also found that, optionally and additionally, by using a device containing nanopores made using cellulose fibers or cellulose nanofibers, the preservation stability of EVs captured from a sample solution increases and the convenience of transfer of EVs increases.

That is, it is an object of the disclosure in the present application to provide a device which can capture EVs by a simple working procedure and efficiently. It is also, optionally and additionally, to provide a method for preserving and transferring EVs.

Solution to Problem

The disclosure in the present application relates to devices, preservation methods, and transfer methods, shown below.

(1) A device to be used for capturing extracellular vesicles in a sample solution, the device comprising:
  a nanostructure body capable of capturing an extracellular vesicle.

(2) The device according to (1) above, wherein the nanostructure body comprises at least one selected from:
a nanowire;
a structure body made using cellulose fibers; and
a structure body made using cellulose nanofibers.
(3) The device according to (2) above, wherein the nanostructure body is a structure body made using cellulose nanofibers.
(4) The device according to (3) above, wherein the gap between the cellulose nanofibers of the nanostructure body is greater than or equal to 1 nm and smaller than 1000 nm.
(5) The device according to (2) above, wherein the nanostructure body comprises at least one selected from:
a structure body comprising nanopores made using cellulose fibers, and having an average size greater than or equal to 10 nm and smaller than 1000 nm, and
a structure body made using cellulose nanofibers and comprising nanopores having an average size greater than or equal to 10 nm and smaller than 1000 nm.
(6) The device according to any one of (1) to (5) above, wherein the sample solution is a non-invasive biological sample solution.
(7) The device according to (6) above, wherein the biological sample solution is saliva.
(8) A method of preserving extracellular vesicles, the preserving method comprises:
an extracellular vesicle capture step of bringing a device of (5) above and a sample solution into contact with each other, to capture an extracellular vesicle in the sample solution in the device;
a drying step of removing a liquid of the sample solution which impregnated the device; and
a preserving step of preserving the device which is dried in the drying step and has captured the extracellular vesicle.
(9) The preserving method according to (8), wherein the preserving step is carried out at room temperature.
(10) A method of transferring an extracellular vesicle, the transfer method comprises:
an extracellular vesicle capture step of bringing a device of (5) above and a sample solution into contact with each other, to capture an extracellular vesicle in the sample solution in the device;
a drying step of removing a liquid of the sample solution which impregnated the device; and
a transfer step of transferring the device which is dried in the drying step and has captured the extracellular vesicle.
(11) The transfer method according to (10) above, wherein the transfer step is carried out at room temperature.
(12) The device according to (1) above, wherein the nanostructure body capable of capturing an extracellular vesicle is a nonwoven fabric including a cellulose fiber.
(13) The device according to (12) above, wherein the cellulose fiber is a cellulose nanofiber.

DETAILED DESCRIPTION OF A PREFERRED EMBODIMENT

Advantageous Effects of Invention

By the devices disclosed in the present application, EVs in a sample solution can be captured and subsequently miRNA can be directly extracted from the EVs captured in the device.

Also, as an optional additional effect, by using a device including nanopores made using cellulose fibers or cellulose nanofibers, the preservation stability of EVs increases and the convenience of transfer of EVs increases.

BRIEF DESCRIPTION OF DRAWINGS

Figure 1:
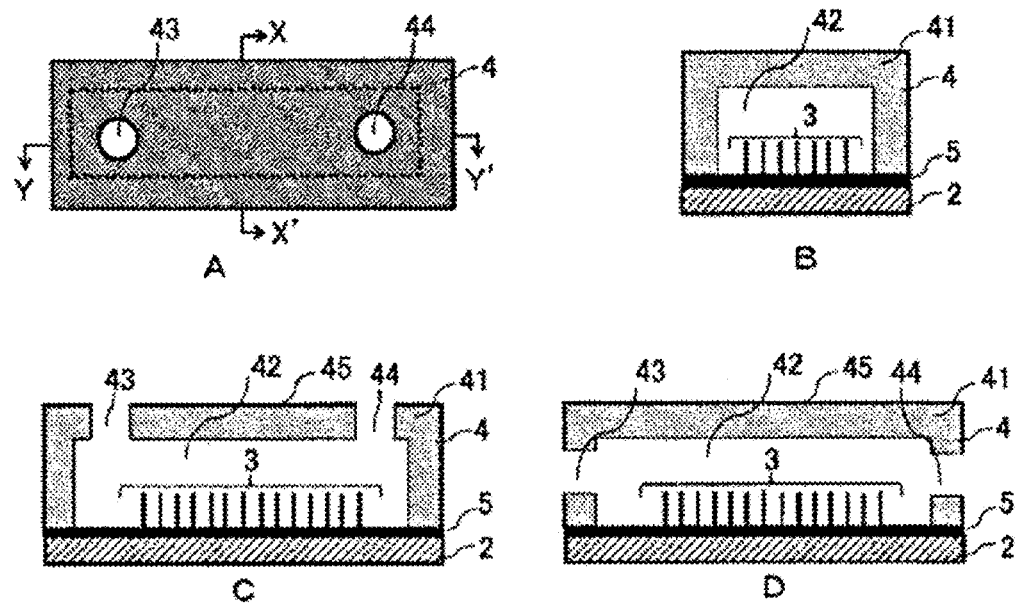
FIGS. 1-14 depict embodiments as described herein.
Figure 2:
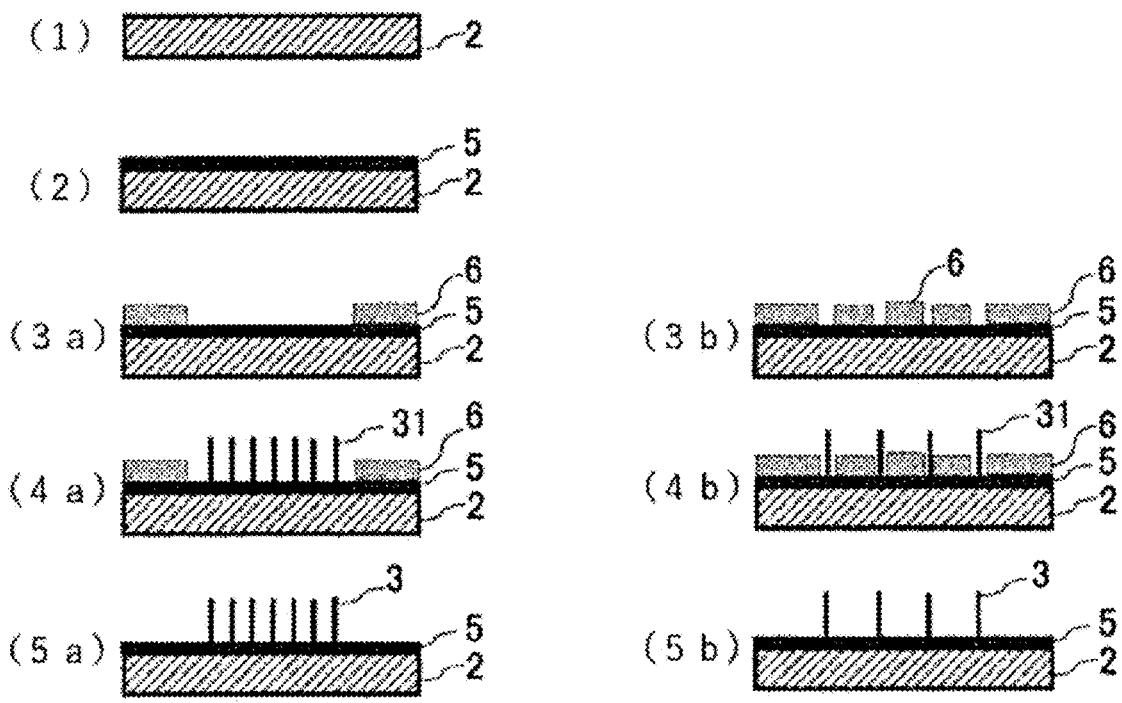
Figure 3:
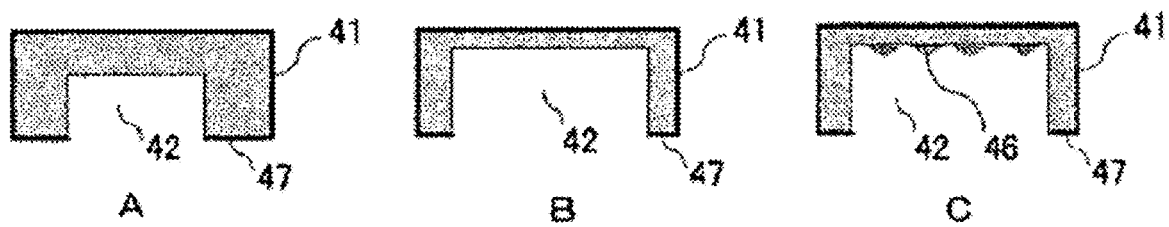
Figure 3:
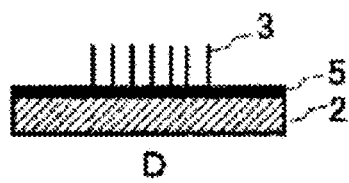
Figure 4:
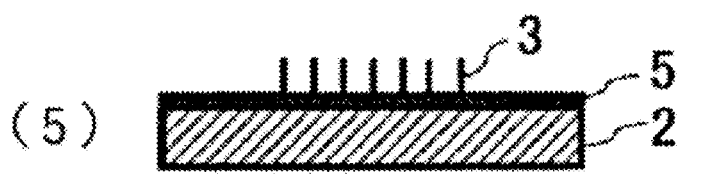
Figure 4:
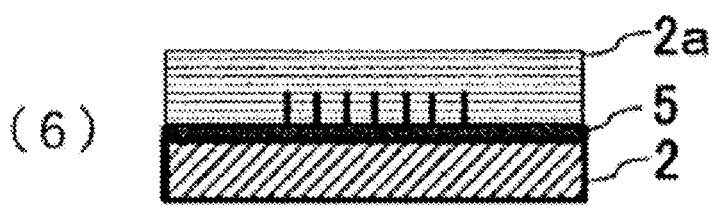
Figure 4:
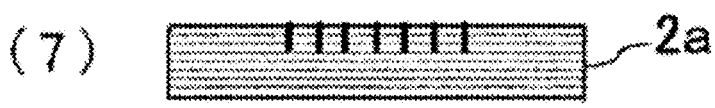
Figure 4:
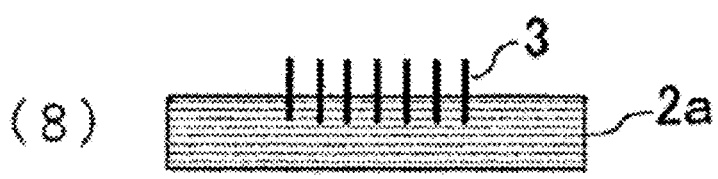
Figure 5:
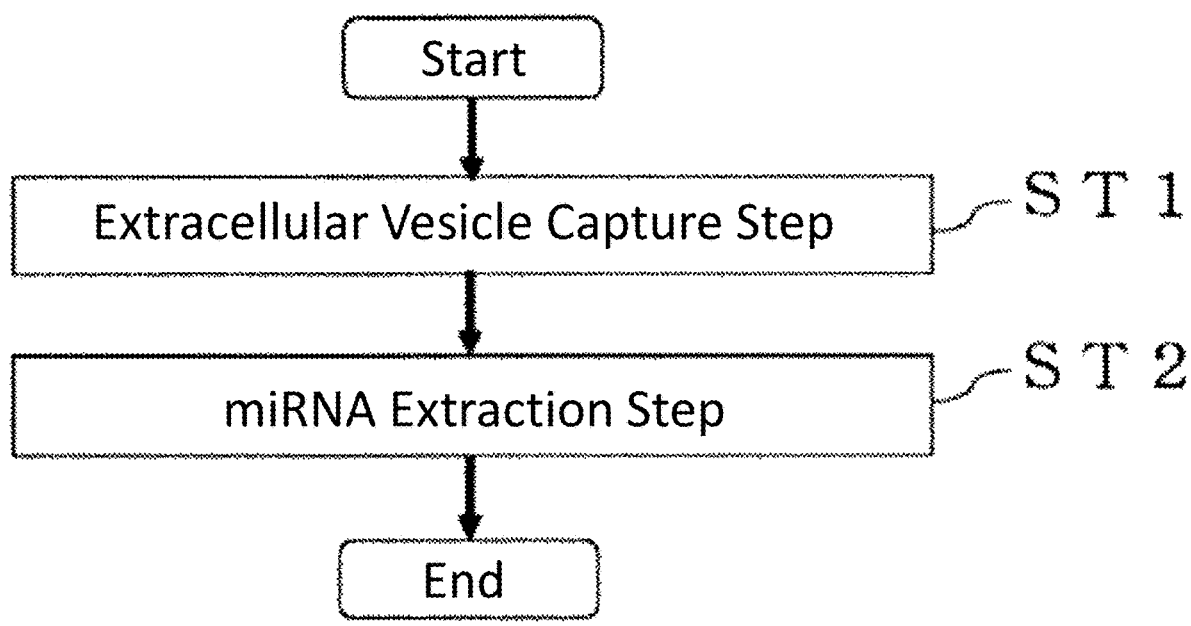
Figure 6:
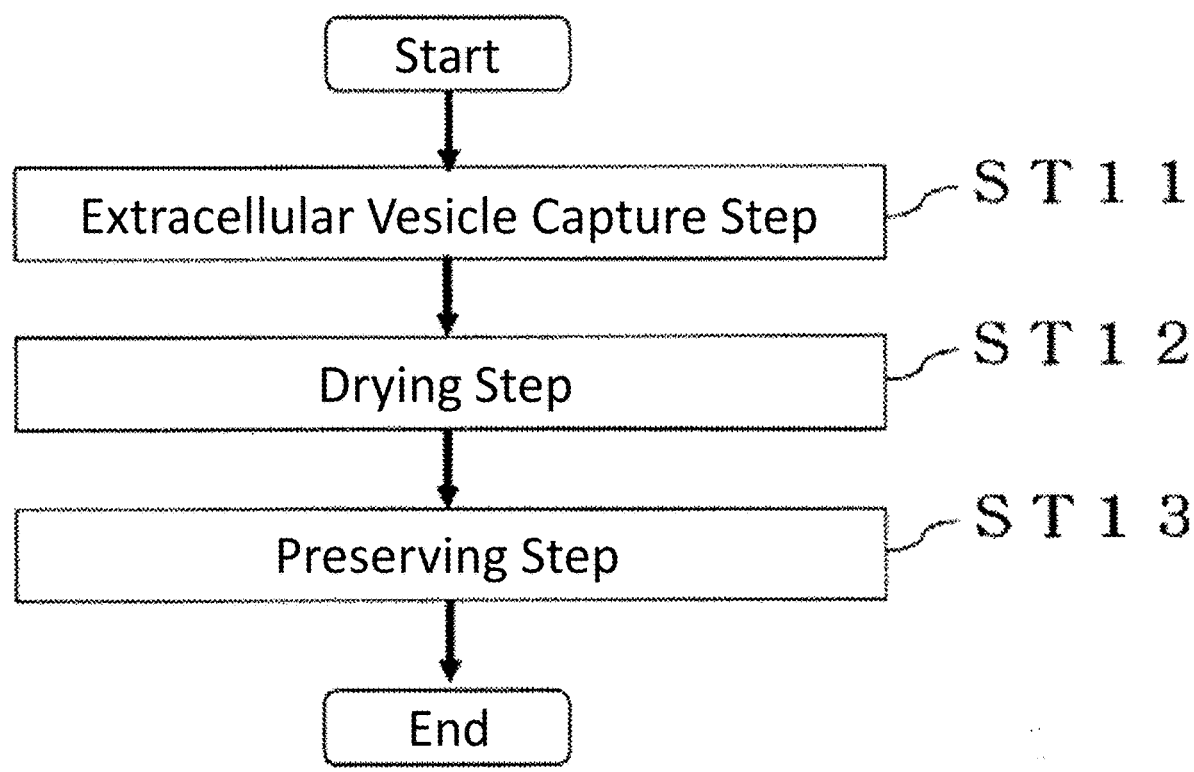
Figure 7:
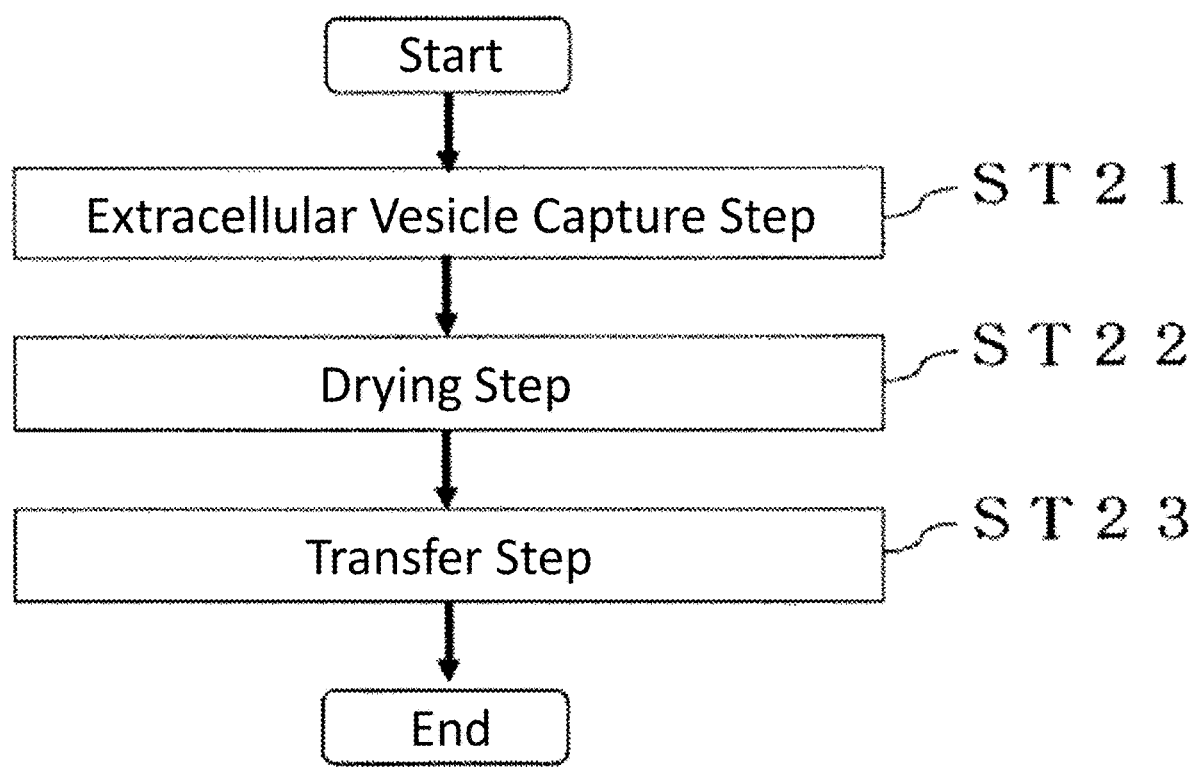
Figure 8:
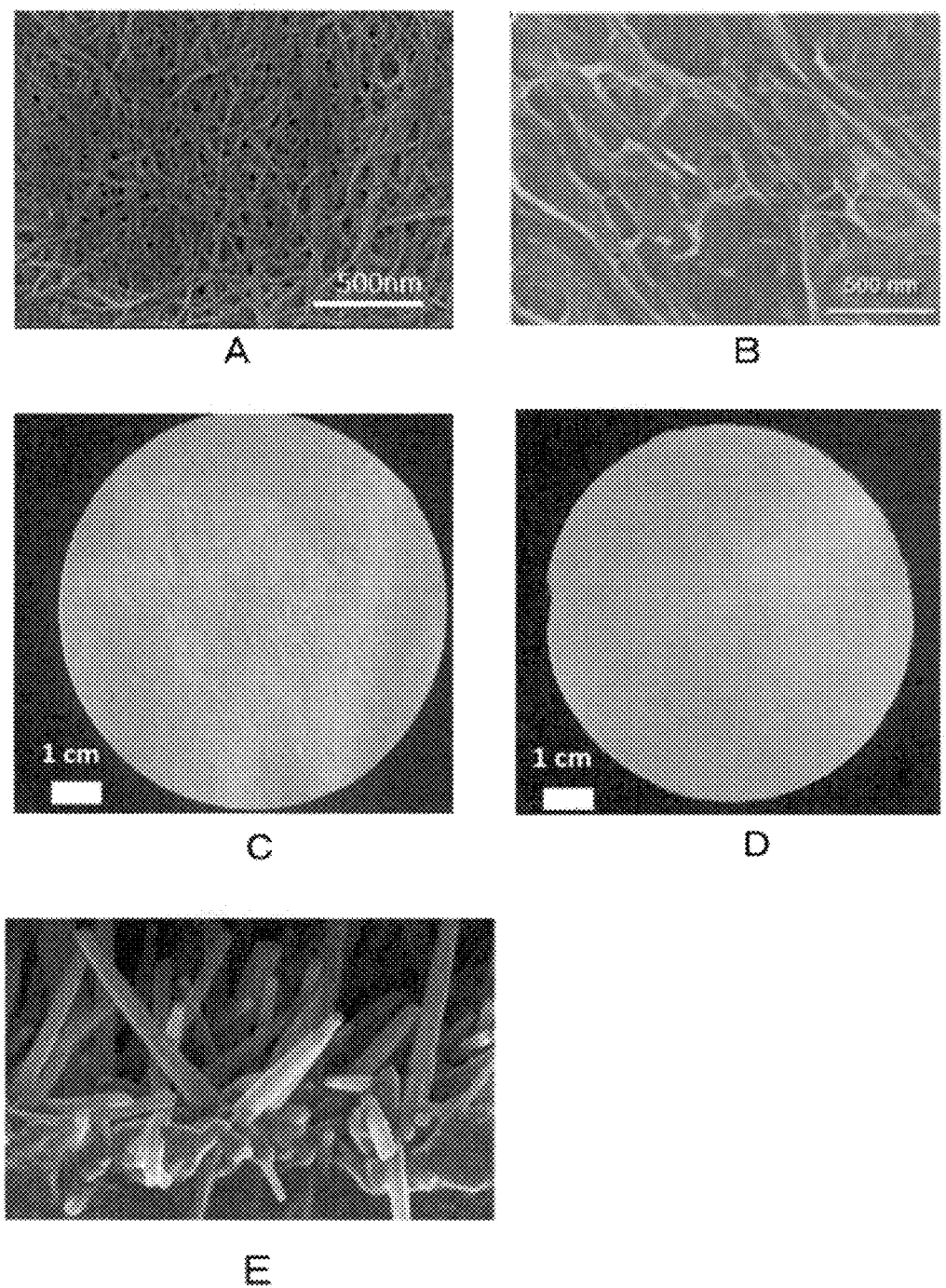
Figure 9:
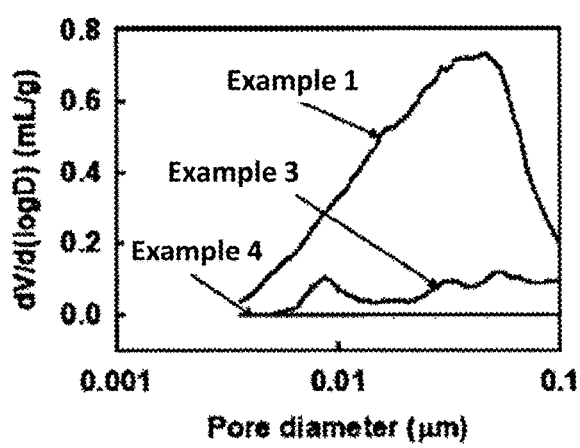
Figure 9:
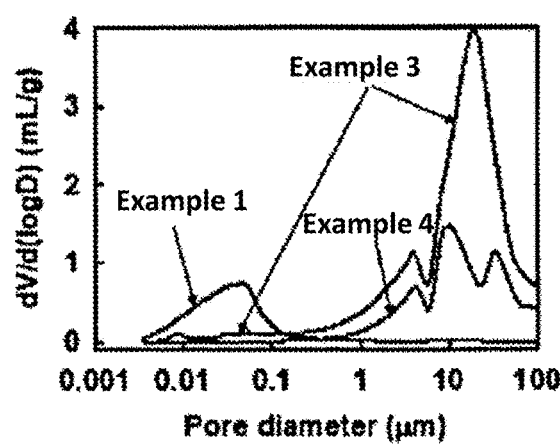
Figure 11:
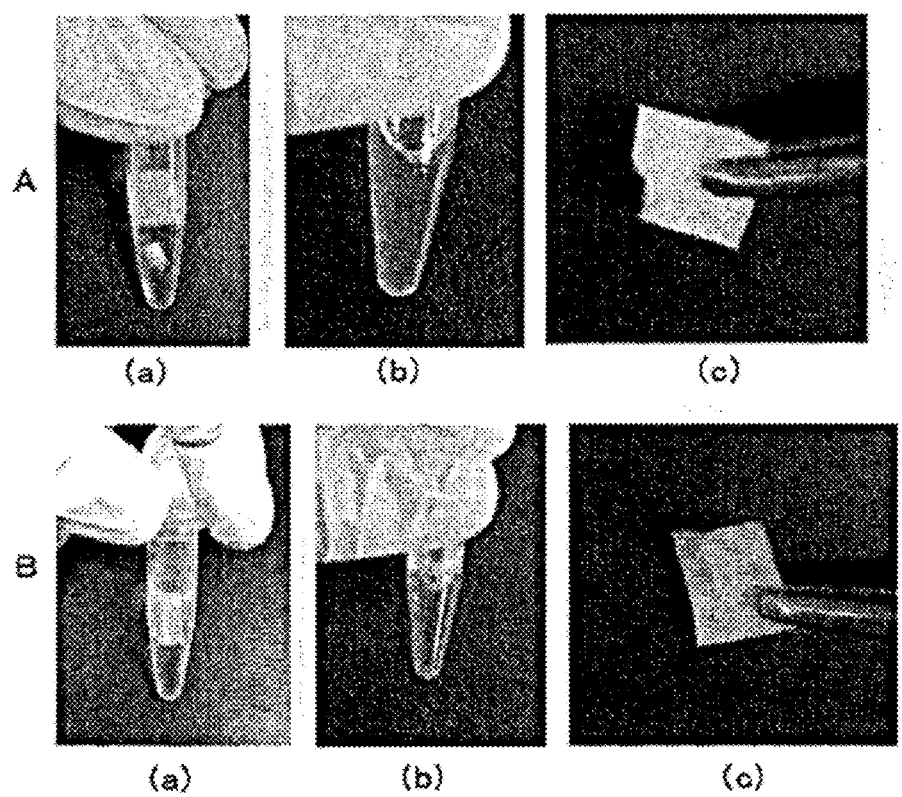
Figure 12:
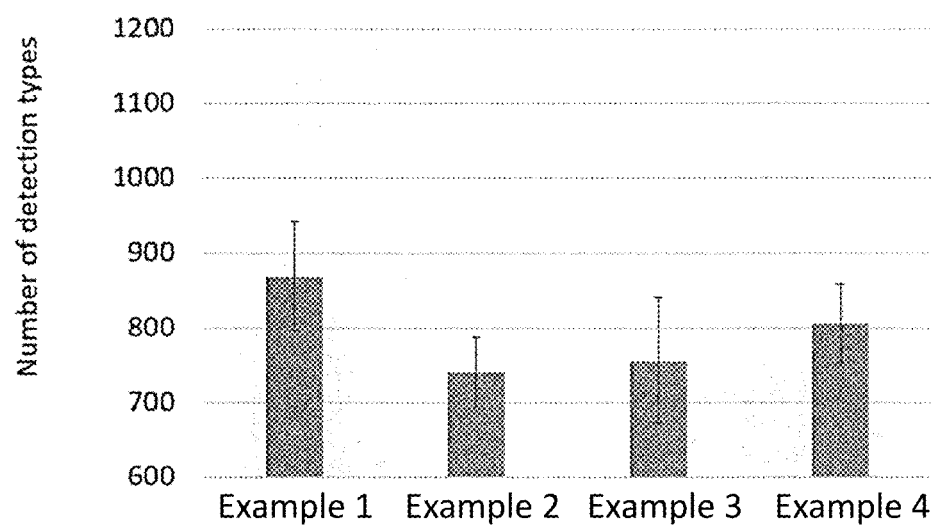
Figure 13:
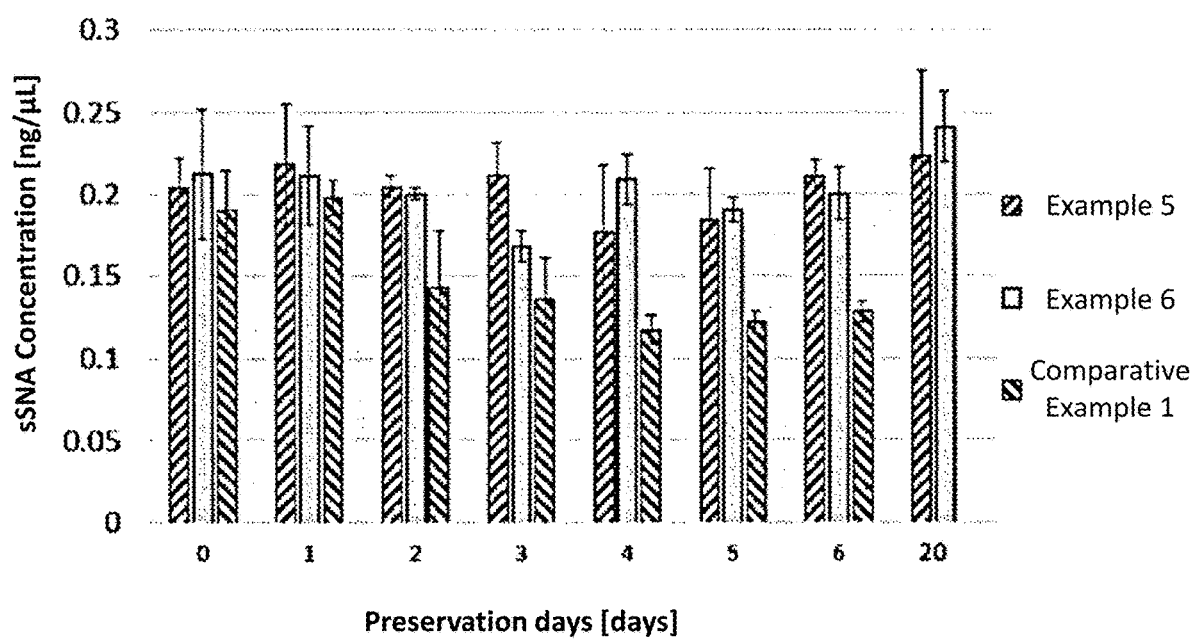
Figure 14:
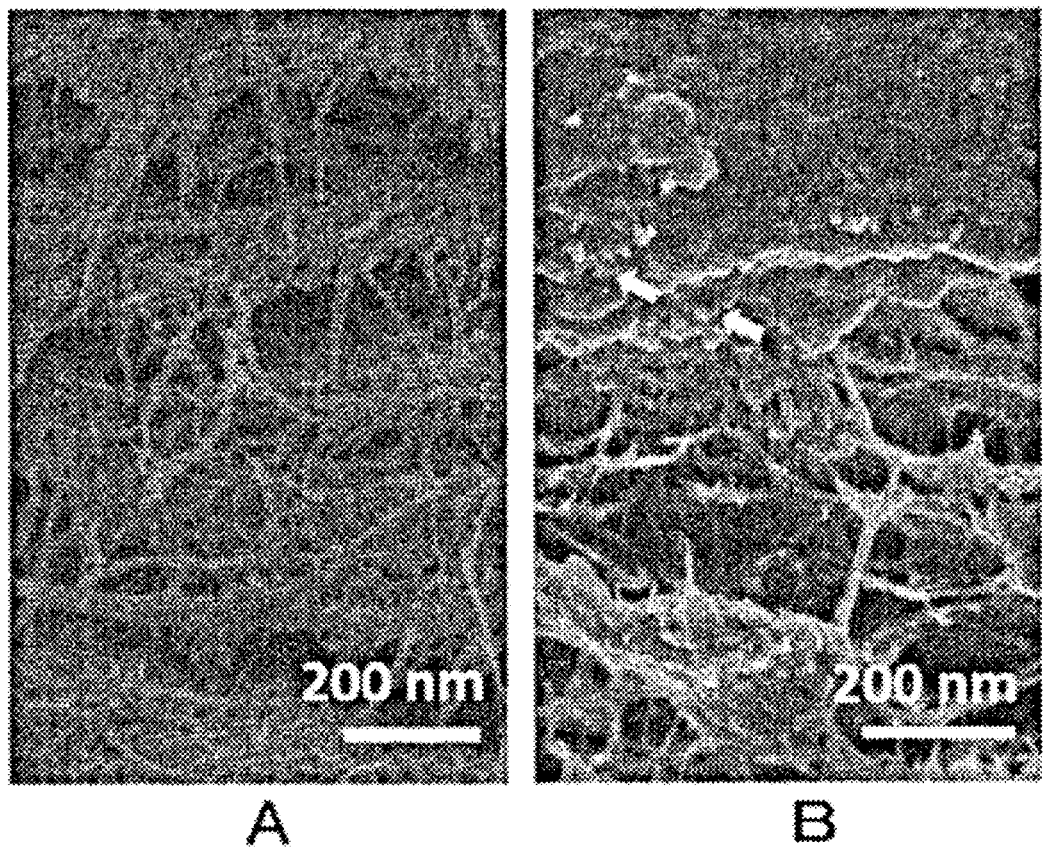

FIGS. 1A to 1C show an example of device 1 according to the third embodiment of the present invention.
FIG. 2 shows a manufacturing process of device 1a having nanowires 3 formed on the first surface of the substrate 2 as an example of device 1 according to the third embodiment.
FIGS. 3A to 3C show various aspects of cover member 4.
FIG. 3D shows substrate 2 having nanowires formed on the first surface.
FIG. 4 explains an example of a manufacturing process of device 1b according to the fourth embodiment.
FIG. 5 shows a flowchart of the extraction method according to the first embodiment.
FIG. 6 shows a flowchart of an embodiment of the preserving method.
FIG. 7 shows a flowchart of an embodiment of the transfer method.
FIGS. 8A to 8E are photographs in substitution for drawing of devices manufactured in Examples 1 to 5, respectively.
FIG. 9 shows a graph showing the results of the size distribution of the pores of the film manufactured in Examples 1, 3 and 4, measured by mercury intrusion method.
FIG. 9A shows a graph showing the distribution for the scale of the pore size of 1 nm to 100 nm, and FIG. 9B shows a graph showing the distribution for the scale of the pore size of 1 nm to 100 µm.
FIGS. 10A and 10B are photographs in substitution for drawing showing (a) a photograph of the centrifuge tube after the device was removed from the centrifuge tube after the miRNA extraction, and (b) a photograph of the device removed from the centrifuge tube.
FIGS. 11A and 11B are photographs in substitution for drawing showing (a) a photograph of the centrifuge tube immediately after completion of miRNA extraction step; (b) a photograph of the centrifuge tube after the device was removed from the centrifuge tube after the miRNA extraction; and (c) a photograph of the device removed from the centrifuge tube.
FIG. 12 shows a graph showing the types of miRNA contained in the miRNA extract solution extracted using the devices of Examples 1 to 4.
FIG. 13 shows a graph showing the analysis results of Examples 5 and 6, and Comparative Example 1.
FIG. 14 is a photograph in substitution for drawing, where FIG. 14A shows a photograph of the SEM before saliva is dropped in Example 5.
Further, FIG. 14B shows a SEM-photograph after saliva was dropped in Example 5.

DESCRIPTION OF EMBODIMENTS

Hereinafter, the device will be described in detail with reference to the drawings. Note that, in the present specification, members having the same kind of functions are denoted by the same or similar reference numerals. Repeated descriptions of the same or similar numbered members may be omitted.

The devices disclosed in this application are characterized in that they comprise nanostructure bodies capable of capturing EVs. In this specification, the term "nanostructure body" means a structure body capable of adsorbing EVs by interaction, and enhancing the adsorption efficiency of EVs by increasing the specific surface area as compared with the minimum area of materials of the same kind and in the same amount.

The nanostructure body can be manufactured, for example, by using a material having fine pores (nanopores), or by aggregating (clustering) fine fibers (wires), or the like. As used herein, "nanopore" means a nano-sized opening or a fiber interval having an average size of 10 nm or greater and smaller than 1000 nm. In addition, when "with nanopores" or "including nanopores" is described, it means that the pores are distributed in the nano order (1 nm or greater and smaller than 1000 nm) and the average size of only the pores in the nano order is 10 nm or greater and smaller than 1000 nm. Therefore, the pores of the micro order (1 µm or greater and smaller than 1000 µm) may be included as long as they include "nanopores", but the pores of the micro order do not serve as a basis for calculating the average size of the "nanopores". When "no nanopore" is described, it means that the pores of the nano order are not included, or the average size of only the pores of the nano order is excluded from the average size of the "nanopore". The shape of the device including the nanostructure body is not particularly limited, and may be any of, for example, a film shape; a string shape; a three-dimensional shape such as a cylindrical shape, a prismatic shape, or an irregular shape. Embodiments of the film-like and nanowire-based devices are described below, but the following device embodiments are merely illustrative and are not limited to the embodiments illustrated below, as long as they satisfy the definition of "nanostructure body". The average size of the nanopores can be measured by mercury intrusion.

First Embodiment of Device

The first embodiment of the device uses a film manufactured using cellulose nanofibers as the nanostructure body. To obtain cellulose nanofibers, wood fibers (cellulose fibers) are first removed from wood chips and pulped. This cellulose fiber is composed of myriad cellulose nanofibers in bundles. Next, in the presence of a TEMPO catalyst, the cellulose fibers are collided with each other at a high pressure in a solvent to dissolve the bundled cellulose fibers, thereby obtaining cellulose nanofibers. Note that the method for manufacturing the cellulose nanofibers described above is merely exemplary, and other methods may be used. The device according to the first embodiment can be manufactured by subjecting a solvent containing the obtained cellulose nanofibers to suction filtration, whereby the cellulose nanofibers are aggregated and formed into a film by surface tension. Examples of the solvent for dispersing the cellulose nanofibers include water and the like. In some embodiments, the manufactured film can be a nonwoven fabric.

Note that, in the device according to the first embodiment, the cellulose nanofibers of the manufactured film may have gaps (nanopores). By adjusting the size of the nanopores, it is possible to improve the capture efficiency of EVs. The average size of the nanopores can, for example, have a lower limit value of 10 nm or greater, 15 nm or greater, 20 nm or greater, 25 nm or greater, or 30 nm or greater, and an upper limit value of smaller than 1000 nm, 500 nm or smaller, 200 nm or smaller, or 100 nm or smaller. When the device according to the first embodiment is used for the preserving method or the transfer method of EVs, it is preferable that the EVs are confined in the nanopores as shown in examples described later. Since there is a distribution in the size of the nanopores, even when the average size of the nanopores is 10 nm, there exist nanopores of size that can confine EVs. However, in order to confine more EVs in the nanopore, the lower limit of the average size of the nanopore may be, for example, 40 nm or greater, 45 nm or greater, 50 nm or greater, 60 nm or greater, or the like. The average size of the nanopores can be measured by mercury intrusion.

The nanopores can be formed by adding a liquid having a low surface tension (hereinafter, sometimes referred to as a "low surface tension solvent") to the cellulose nanofibers in a wet state, which are aggregated by suction filtration, followed by suction, and replacing and drying the solvent contained in the aggregated cellulose nanofibers with the low surface tension solvent. The size of the nanopores can be adjusted by varying the low surface tension solvent to be applied. The surface tension of the low surface tension solvent is not particular limited as long as it is smaller than the surface tension of water (20° C., 72.75 mN/m) and the nanopores can be manufactured. For example, the surface tension at 20° C. may be 35 mN/m or smaller, 30 mN/m or smaller, 25 mN/m or smaller, 20 mN/m or smaller, or the like. Specific examples of the low surface tension solvent include tertiary butyl alcohol (20.7 mN/m), ethanol (22.55 mN/m), isopropanol (20.8 mN/m), and the like. The formation and size adjustment of the nanopores described above are merely examples, and the formation and size adjustment of the nanopores may be performed by other methods. For example, by changing the high pressure treatment conditions for dissolving the cellulose fibers or by changing the cellulose raw material such as the type, bacteria, and ascidia of the pulp, the width of the cellulose nanofibers and the size of the nanopores may be adjusted. When dispersing nanopores, more EVs are captured, and many types of miRNA can be analyzed.

Second Embodiment of Device

The second embodiment of the device differs from the first embodiment in that a film manufactured using cellulose fibers (pulp) are used as the nanostructure body instead of cellulose nanofibers. The device according to the second embodiment may be manufactured by the same procedure as in the first embodiment of the device, except that the cellulose fibers (pulp) are dispersed in a solvent instead of the cellulose nanofibers. The gap between the cellulose fibers and the gap between the cellulose nanofibers present on the cellulose fiber surface can also be manufactured and the size can be adjusted in the same manner as in the first embodiment. Since the width of the cellulose nanofibers is about 3 nm to 100 nm, nanopores having a size of about 1 nm to 200 nm are formed. On the other hand, the width of the cellulose fiber is about 20 µm to 40 µm. Thus, unlike the first embodiment, the size of the gap is multi-scaled, on the order of nm to µm, on the order of about 1 nm to 200 nm, and on the order of about 1 µm to 100 µm.

In the device according to the first and second embodiments, the manufactured film can be cut into an appropriate size and used as it is. Alternatively, a device which has been cut may be attached into a centrifuge tube or the like used in the miRNA extraction step described later, it can be sticked to a mask to capture EVs in the cough, and it can be sticked to a towel or the like to capture EVs in the sweat. Also, although the first and second embodiments of the device are film-like, they may be of other shapes. For example, in the case of forming a thread (string), a mold in which a groove is formed in the form of a thread (string) (suction filtration filter) may be used when suction filtration is performed. Further, a solvent in which cellulose (nano) fibers are dispersed may be injected into a coagulation bath such as acetone and spun. In the case of forming a predetermined three-dimensional shape, suction filtration may be performed using a mold (suction filtration filter) in which a predetermined shape is formed. In addition, when forming an irregular three dimensional shape is formed, first, a solvent in which cellulose (nano) fibers are dispersed is charged into only a part of a suction filtration filter, and a mass of cellulose (nano) fibers aggregated is manufactured by suction filtration, and the manufacture of the mass of aggregated cellulose (nano) fibers is repeated, and thereby an irregular shape of three dimensional nanostructure body can be manufactured. Also, a solvent in which cellulose (nano) fibers are dispersed can be placed in a container having a desired shape, and a freeze-drying treatment can be performed, to manufacture a nanostructure body having a three-dimensional shape. Further, the device may be manufactured of only cellulose (nano) fibers, or a filler or the like may be added as long as it does not impair the purpose of the present disclosure. Examples thereof include the addition of a filler such as polyamidoamine epichlorohydrin as a wet paper force enhancer, the addition of nanowires (for nanowires, see the third embodiment described later) alone, and the like.

Third Embodiment of Device

The third embodiment of the device uses nanowires as a device. FIGS. 1A to 1D illustrate an example of devices 1 according to the third embodiment. FIG. 1A shows a top view of device 1a, FIG. 1B shows a X-X' cross-sectional view, and FIG. 1C shows a Y-Y' cross-sectional view. Further, FIG. 1D shows a cross-sectional view of a modification of the embodiment shown in FIG. 1C. The device 1a includes at least a substrate 2, a nanowire 3, and a cover member 4, and the device 1a shown in FIG. 1B to FIG. 1D (hereinafter, the descriptions common to FIG. 1 may simply be described as "FIG. 1". The same applies to the following paragraphs.) includes a catalyst layer 5 for forming the nanowires 3. The device 1a has the catalyst layer 5 formed on the substrate 2 for forming the nanowires 3, the nanowires 3 are formed on the catalyst layer 5. In this specification, the "first surface" means the outermost surface of the surface of the side on which the nanowires 3 of the substrate 2 are formed. Therefore, as described later, when the "first surface" of the substrate 2 and the "second surface" of the cover member are described as being in liquid-tight contact with each other, the member of the "first surface" becomes the substrate 2, the catalyst layer 5, or the coating layer, according to the manufacturing method. Furthermore, in some cases the nanowires are grown on the "first surface" to be in close contact with the "second surface" of the cover member, in which case the flat portion at the base of the nanowires becomes the "first surface". Also, as used herein, the term "tip" of a nanowire refers to the end of the nanowire away from the first surface of the substrate 2, of both ends of the nanowire, and the end of the nanowire on the first surface side of the substrate 2 is referred to herein as "end."

The cover member 4 includes a cover member base 41 and a flow path 42 formed in the cover member base 41. In this specification, the "second surface" means a surface of the cover member base material 41 on the side where the flow path 42 is formed (in the case where the opening portion of the flow path 42 is a virtual plane, a surface following the virtual plane). In the example shown in FIG. 1B, the surface of the cover-member base material 41 in contact with the catalytic layer 5 corresponds to the second surface. In the example shown in FIG. 1C, the cover member 4 includes a sample introduction hole 43 and a sample collection hole 44. As shown in FIG. 1C, the sample introduction hole 43 and the sample collection hole 44 are formed in the cover member base material 41 so as to penetrate the flow path 42 and the surface 45 opposed to the second surface. Moreover, the example shown in FIG. 1C shows an example of introducing and collecting the sample solution from above of the device 1a, but the positions of the sample introduction hole 43 and the sample collection hole 44 are not particularly limited as long they can collect the sample solution which was input and passed the region with formed nanowires 3, can be collected after passing there. For example, as shown in FIG. 1D, the sample introduction hole 43 and the sample collection hole 44 may be formed in the side wall of the flow path 42.

The device 1a according to the third embodiment can be manufactured using a photolithography technique. FIG. 3 shows an example of the device 1 according to the third embodiment, for explaining an example of a manufacturing process of the device 1a having the nanowires 3 formed on the first surface of the substrate 2. FIG. 2 illustrates a cross-sectional view of X-X' in FIG. 1A.

(1) Prepare a Substrate 2.

(2) Form the catalyst layer 5 on the substrate 2, by sputtering particles for manufacturing nanowire 3 by ECR (Electron Cyclotron Resonance) sputtering, or the catalyst ECR sputtering, depositing by EB (Electron Beam) deposition, PLD (Pulsed Laser Deposition), ALD (Atomic Layer Deposition).

In this specification, the term "catalyst layer" means "particle" or "layer" of "catalyst" for manufacturing nanowires.

(3a, 3b) Apply resist 6 for photolithography, and pattern by photolithography the location where the nanowires 3 are to be grown. The patterning of the photolithography may be formed in a pattern in which the nanowires 3 are to be grown. For example, if the nanowires 3 are to be grown at random, it may be patterned so that the catalyst layer 5 of the region forming the nanowires 3 on the substrate 2 is all exposed (see 3a). Further, when the nanowires 3 are to be grown at predetermined intervals, a patterning or a drawing by photolighography may be done so as to expose the catalyst layer 5 in the shape of dots at predetermined intervals (see 3b). After patterning or drawing by photolithography, the resist 6 of the patterned or drawn portion is developed and removed.

(4a, 4b) the resist is removed to grow the nanowires 3 from where the catalyst layer 5 is exposed.

(5a, 5b) by removing the remaining resist, it is possible to manufacture a substrate 2 having nanowires 3 formed on the catalyst layer 5 formed on the first surface.

FIGS. 3A to 3C show various aspects of the cover member 4. The cover member 4 can be easily manufactured by cutting the second surface 47 of the cover member base material 41 or pressing a convex mold against the material of the cover member base material 41. When the cover member 4 is manufactured by pressing a convex mold, the sample introduction hole 43 and the sample collection hole 44 may be formed by using a biopsy trepan, an ultrasonic drill, or the like after transfer. By changing the cutting area and the shape of the mold of the cover member 4, for example, as shown in FIG. 4A and FIG. 4B, the cross-sectional area of the flow path 42 can easily be changed. As shown in FIG. 4C, a non-planar area 46 may be formed for generating turbulence in the sample solution passing through on any surface of the flow path 42. The nonplanar area 46 is not particularly limited as long as it can generate turbulence in the sample solution passing therethrough, and for example, a convex portion or the like may be formed. The cover members 4 can be prepared, in a plurality of different types in the cross-sectional area and the shape of the flow path 42.

Then, the substrate 2 (FIG. 3D) having nanowires 3 formed on the first surface prepared by the process shown in FIG. 2 can be covered by the cover member 4 having a flow path 42 of a desired cross-sectional area and shape, to manufacture a device 1a.

The substrate 2 is not particularly limited as long as the catalyst layer 5 can be laminated. Examples include silicon, quartz glass, Pyrex (registered trademark) glass, and the like.

Regarding the catalyst layer 5, as the particles for preparing the nanowires 3, for example, ZnO. Examples of the catalyst for manufacturing the nanowires 3 include gold, platinum, aluminum, copper, iron, cobalt, silver, tin, indium, zinc, gallium, chromium, oxides thereof, and the like.

The resist 6 for photolithography is not particularly limited as long as it is commonly used in the semiconductor field, such as OFPR8600LB, SU-8 and the like. Further, as the removing liquid of the resist 6, there is no particular limitation as long as it is a removing liquid common in the semiconductor field such as dimethylformamide and acetone.

The nanowires 3 may be grown from the catalyst layer 5 by a known method. For example, when using ZnO fine particles as the catalyst layer 5 they can be manufactured using a hydrothermal synthesis method. Specifically, by immersing the heated substrate 2 in a precursor solution in which zinc nitrate hexahydrate ($Zn(NO_3)_2 \cdot 6H_2O$) and hexamethylenetetramine ($C_6H_{12}N_4$) are dissolved in deionized water, ZnO nanowires 3 can be grown from a portion where ZnO particles (catalyst layer 5) are exposed.

When a catalyst is used as the catalyst layer 5, the nanowires 3 can be manufactured in the next step. (a) Using materials such as $SiO_2$, $Li_2O$, $MgO$, $Al_2O_3$, $CaO$, $TiO_2$, $Mn_2O_3$, $Fe_2O_3$, $CoO$, $NiO$, $CuO$, $ZnO$, $Ga_2O_3$, $SrO$, $In_2O_3$, $SnO_2$, $Sm_2O_3$, $EuO$, etc., the core nanowires are formed by a physical vapor deposition method such as pulsed laser deposition, VLS (Vapor-Liquid-Solid) method. (b) Using $SiO_2$, $TiO_2$ or the like, sputtering, EB (Electron Beam) deposition, PVD (Physical Vapor Deposition), by a common deposition method such as ALD (Atomic Layer Deposition), to form a coating layer around the core nanowires. Note that the coating layer of (b) above is not essential and may be implemented as necessary.

The diameter of the nanowires 3 may be appropriately adjusted according to the purpose. When forming using ZnO fine particles, the diameter of the nanowire 3 may be changed by the size of the ZnO fine particles. When forming a coating layer on the manufactured nanowires 3, the diameter can be appropriately adjusted by changing the deposition time when forming the coating layer.

As a material for manufacturing the cover member 4, there is no particular limitation as long as it can be cut or transfer the mold. Examples include: thermoplastic resins such as polyethylene, polypropylene, polyvinylchloride, polyvinylidene chloride, polystyrene, polyvinyl acetate, polytetrafluoroethylene, ABS (acrylonitrile butadiene styrene) resins, AS (acrylonitrile styrene) resins, acrylic resins (PMMA), and the like; thermosetting resins such as phenolic resins, epoxy resins, melamine resins, urea resins, unsaturated polyester resins, alkyd resins, polyurethanes, thermosetting polyimides, and silicone rubbers, and the like.

The examples shown in FIGS. 1 to 3 are merely exemplary of the device 1, there is no particular limitation as long as the nanowires are formed on the substrate 2. For example, nanowires may be formed in the flow paths formed on the substrate 2 by the procedure described in WO 2015/137427.

Fourth Embodiment of Device

The device 1b according to the fourth embodiment is different from the device 1a according to the third embodiment in that the end portion of the nanowire 3 is embedded in the first surface of the substrate 2a and in that the material for manufacturing the substrate 2a is different from the device 1a according to the third embodiment, and is otherwise the same as the device 1a according to the third embodiment.

FIG. 4 is a drawing for explaining an example of a manufacturing process of the device 1b according to the fourth embodiment;

(5) Prepare a substrate 2 having formed with nanowires 3 formed on the first surface, which was manufactured in the device 1a according to the third embodiment, as a mold.

(6) Apply the material forming the substrate 2a to the mold.

(7) By peeling the substrate 2a from the mold, form substrate 2a having a portion of the nanowires 3 embedded in the first surface.

(8) By further growing the nanowires 3 embedded in the first surface of the substrate 2a, manufacture the substrate 2a having the end portion of the nanowires 3 embedded in the first surface. The nanowires 3 can be grown by the same procedure as in the first embodiment. Though not shown, the device 1b can be manufactured by covering the substrate 2a with the cover member 4 manufactured in the same procedure as in the third embodiment.

The material for forming the substrate 2a is not particularly limited as long as the nanowires 3 can be embedded, and for example, a material similar to that of the cover member 4 can be used.

Next, embodiments of methods of capturing EVs using the above-described devices and methods of extracting miRNA after capture (hereinafter, sometimes abbreviated as "extraction method") will be described.

First Embodiment of Extraction Method

Referring to FIG. 5, the first embodiment of the extraction method will be described. FIG. 5 shows a flowchart of the extraction method according to the first embodiment. The first embodiment of the extraction method includes an extracellular vesicle (EVs) capture step (ST1), a miRNA extraction step (ST2)

In the extracellular vesicle (EVs) capture step (ST1), by contacting the sample solution with a device capable of capturing EVs, EVs in the sample solution are captured in the device. In the miRNA extraction step (ST2), by contacting the device that captured EVs with the EVs disruption solution, EVs are disrupted and miRNA are extracted from the EVs into the disruption solution.

The sample solution is not particularly limited as long as it contains EVs and may be a biological sample solution such as blood, lymph, bone marrow fluid, semen, breast milk, amniotic fluid, urine, saliva, nasal mucus, sweat, tears, bile fluid, cerebrospinal fluid, or the like. Further, examples of the sample solution other than biological sample solutions include a cell culture supernatant, a sample solution for an experiment in which EVs are added to a medium or a buffer solution, and the like. When a biological sample solution is used as a sample solution, a non-invasive sample solution such as urine, saliva, nasal mucus, sweat, or tear is preferred in consideration of reduction in patient burden.

Note that, as shown in the examples described later, by analyzing miRNA extracted using the device disclosed in the present application was analyzed, many types of miRNA could be analyzed. In other words, using the devices disclosed in the present application, even a trace amount of miRNA that could not be analyzed by conventional methods could be analyzed. Therefore, when the device disclosed in the present application is used, it is possible to extract miRNA in a small amount if it is a sample solution of the same type. In addition, in order to fractionate and collect EVs by ultracentrifugation, a sample solution of about several milliliters is required. However, there are also biological sample solutions, such as saliva and tears, for example, in which it becomes a great burden for the patient to collect a quantity of several milliliters. In the first embodiment of the extraction method, by using the device disclosed in the present application, since miRNA can be extracted even if the amount of the sample solution is small as compared with the conventional ultracentrifugation methods, it is particularly useful for extracting miRNA contained in the EVs in saliva.

There is no particular limitation on the disruption solution of EVs as long as EVs can be disrupted, and for example, a commercially available cell lysis buffer (Cell Lysis Buffer) may be used. Examples of the cell lysis buffer include cell lysis buffer M (manufactured by Fujifilm Wako Pure Chemical Industries, Ltd., 038-21141), RIPA Buffer (manufactured by Fujifilm Wako Pure Chemical Industries, Ltd., 182-02451), and the like. Note that, the time for immersing the device in the disruption solution is not particularly limited as long as miRNA can be taken out by disrupting the EVs. Note that, the above example shows an example in which EVs are first captured in a device, but a solution obtained by disrupting EVs with a disruption solution may be flowed through the device to directly capture miRNA in the device.

Second Embodiment of Extraction Method

The second embodiment of the extraction method differs from the first embodiment of the extraction method in that between the extracellular vesicle (EVs) capture step (ST1) and the miRNA extraction step (ST2) shown in FIG. 5, a device cleaning step of cleaning the device that captured EVs is included, and the other points are similar to those of the first embodiment of the extraction method. The biological sample solution extracted from the living body, for example, saliva, sweat, nasal mucus, and the like, contains RNase, which is an enzyme for decomposing RNAs of foreign substances such as viruses, in order to protect the living body from viruses and the like entering from the outside.

Therefore, when RNase is extracted from a biological sample solution containing miRNA such as saliva, perspiration, and nasal water, there is a risk that RNase is adsorbed on the device during the extracellular vesicle capture step. Then, there is a risk that RNase decomposes miRNA extracted from the EVs when miRNA extraction step is performed on the device to which RNase is adsorbed. Therefore, in the device cleaning step, RNase is removed from the device by cleaning the device that captured EVs. In the device cleaning step, the device that captured EVs may be immersed in a cleaning solution for a predetermined time and washed. The cleaning time is not particularly limited, but if it is too short, there is no cleaning effect, and if it is too long, there arises a problem that the captured EVs are peeled off. For example, in view of the foregoing, the device may be immersed in a cleaning solution for about 1 to 2000 seconds. Examples of the cleaning solution include pure water, PBS, NaCl, physiological saline, and various buffers such as PBS. Note that, when pure water is used as a cleaning solution, it is desirable to set the washing time to be shorter as compared with a buffer or the like so that EVs captured do not burst in the relationship of osmotic pressure.

Embodiment of miRNA Analysis Methods

Embodiments of the analysis methods of miRNA include an analysis step of analyzing miRNA in the disruption solution extracted according to the first or the second embodiment of the extraction method. For analysis of miRNA, known miRNA analysis methods may be used. For example, methods may be used as follows: (1) total RNA including miRNA are extracted using miRneasy Mini Kit (QIAGEN), exhaustive analysis is performed from about 2500 types of miRNA using a 3D-Gene (registered trademark) miRNA chip, chip images are digitized, expression ratios are calculated, variable genes are analyzed, and cluster analysis is performed, (2) miRNeasy Serum/Plasma kit (Qiagen) is used to isolate total miRNA in a disruption solution, miScript II RT Kit (Qiagen) is used to synthesize cDNA, and quantitative real-time PCR is performed.

When a film-like device shown in the first and second embodiments is used as the device, a sample solution may be dropped to the film or the film may be immersed in the sample solution, in the extracellular vesicle capturing step (ST1). When the devices 1a and 1b in which the nanowires are formed on the substrates of the third and fourth embodiments are used as the devices, the sample solution may be introduced through the sample introduction hole in the extracellular vesicle capture step (ST1).

Then, when a film-like device shown in the first and second embodiments is used as the device, the film may be immersed in the disruption solution in the miRNA extraction step (ST2). When a device in which nanowires are formed on the substrate of the third and fourth embodiments is used as the device, the disruption solution may be introduced through the sample introduction hole and the disruption solution containing the extracted miRNA may be collected in the miRNA extraction step (ST2).

In the devices 1a and 1b according to the third and fourth embodiments, the cover member 4 is formed, but the cover member 4 may not be disposed. In such cases, in the extracellular vesicle capture step (ST1), the sample solution may be dropped to the nanowires or the device may be immersed in such a manner that the nanowires contact the container containing the sample solution. In the miRNA extraction step (ST2), the nanowire part may be immersed in the container containing the disruption solution.

Furthermore, in the devices 1a and 1b according to the third and fourth embodiments, the nanowires 3 are formed on the first surface of the substrate, but the nanowires 3 may be used alone. In such cases, in the extracellular vesicle capture step (ST1), the nanowires may be put into tubes or the like in which the sample solution is put, so that the nanowires and the sample solution are contacted with each other.

In addition, in the miRNA extraction step (ST2), after removing the sample solution from the tube, the disruption solution may be introduced into the tube.

Even when the nanowires 3 are used alone as a device, miRNA can be directly extracted from EVs captured by the device. When the nanowires 3 are used alone as a device, for example, the nanowires 3 may be collected from the first surface of the substrate.

As shown in the examples described later, the devices shown in each of the above embodiments are capable of capturing EVs in a sample solution. When the EVs are disrupted by the disruption solution and the extracted miRNA are analyzed comprehensively, if the device is broken by the disruption solution, the residue of the disruption may adversely affect the analysis process in the analysis process. Thus, the device may be durable against the disruption solution, e.g., may have durability against the disruption solution for at least 5 minutes, preferably 30 minutes or more. In the above embodiments, films composed of nanowires or cellulose nanofibers are more preferred devices because they are durable against disruption solution.

Note that the above devices are merely illustrative, and are not limited to the devices of the above embodiments as long as they can adsorb EVs (preferably durable against disruption solution). Such devices include porous materials having a large number of pores at the surface. Specific examples thereof include microporous materials such as activated carbon, zeolite and the like, mesoporous materials such as silicon dioxide (mesoporous silica), aluminum oxide and the like, and macroporous materials such as pumice and the like. In addition, other than porous materials, they include a filter made of molten glass or a polymer.

Embodiment of Method of Preserving Extracellular Vesicles (EVs)

Referring to FIG. 6, an embodiment of the method of preserving extracellular vesicles (EVs) (hereinafter, sometimes simply referred to as a "preserving method") will be described. FIG. 6 is a flowchart of the preserving method according to an embodiment. The embodiment of the preserving method includes an extracellular vesicle capture step (ST11), a drying step (ST12), and a preserving step (ST13)

The extracellular vesicle capture step (ST11) is performed using a device including nanopores, as the device. More specifically, it is performed using a device in which the cellulose nanofibers have gaps (nanopores) shown in the first embodiment, and a device in which the cellulose fibers have gaps (nanopores) shown in the second embodiment. The extracellular vesicle capture step (ST11) may be performed using the same procedure as that of the extracellular vesicle capture step (ST1) of the first embodiment of the extraction method, except that a device including nanopores is used.

In the drying step (ST12), the liquid of the sample solution which impregnated the device is removed. As noted above, using the devices disclosed in this application, the amount of sample solution may be small. Therefore, the drying step may be performed by natural drying in which the liquid is evaporated at room temperature.

In the preserving step (ST13), the device that captured the extracellular vesicles, which was dried in the drying step (ST12), is preserved. As shown in the examples described later, when the extracellular vesicles were analyzed after the preserving step (ST13), there was no significant difference in the preservation temperature, or in the analysis results of the extracellular vesicles between a refrigerated preservation (4° C.) and a room temperature preservation, for example. Therefore, when the collected sample is analyzed at a later date, since it can be preserved in a state of being left at room temperature, the convenience of the sample handling is improved. In this application, room temperature refers to 10° C. to 30° C., for example, and may be higher than 15° C. and at or lower than 30° C.

(Embodiment of Method for Transferring Extracellular Vesicles (EVs))

Referring to FIG. 7, an embodiment of the method for transferring extracellular vesicles (EVs) (hereinafter, sometimes referred to simply as a "transfer method") will be described. FIG. 7 is a flowchart of a transfer method according to an embodiment.

The embodiment of the transfer method includes an extracellular vesicle capture step (ST21), a drying step (ST22), and a transfer step (ST23). The extracellular vesicle capture step (ST21) and the drying step (ST22) are the same as the extracellular vesicle capture step (ST11) and the drying step (ST12) of the above described preservation method. Therefore, the detailed description is omitted in order to avoid duplication of descriptions. In the transfer step (ST23) a device that has captured extracellular vesicles and that has been dried in the drying step (ST22) is transferred. Analysis of miRNA contained in extracellular vesicles is expected to diagnose cancers, but it is often difficult for local medical institutions or individuals to extract and analyze extracellular vesicles from their own biological samples. On the other hand, as described above, in the method for preserving extracellular vesicles disclosed in the present application, the temperature at the time of storage does not significantly affect the analysis accuracy. Therefore, by contacting a biological sample taken from a patient at a local medical institution or the like with the device, drying it, and then transferring the device to a medical institution or the like having an analysis function of extracellular vesicles by mail or the like, a patient residing in any region can receive an appropriate diagnosis. When transferring biological samples, they usually need to be refrigerated or frozen. On the other hand, since the method disclosed in this application can transfer a device at room temperature, the convenience in transferring a sample is greatly improved.

The following examples are provided to explain embodiments disclosed in the present application, but the examples are merely for explanations of the embodiments. It is not intended to limit or restrict the scope of the inventions disclosed in this application.

EXAMPLES

Device Fabrication

Example 1

A film-like device having nanopores was manufactured from cellulose nanofibers by the following procedure.

(1) 400 mg of nanocellulose having a width of 15 to 100 nm obtained by treating conifer bleached kraft pulp with a wet pulverization equipment (Star Burst HJP-25005E) manufactured by SUGINO MACHINE Ltd., was introduced into 200 mL of water to obtain a nanocellulose aqueous dispersion.

(2) The above nanocellulose aqueous dispersion was filtered and dehydrated using a filtration device (KG-90, Advantek Toyo Roshi Kaisha, Ltd.) and an aspiration device (Aspirator AS-01, AS ONE Corporation) and through a hydrophilic polytetrafluoroethylene (PTFE) membrane filter (H020A090C, Advantek Toyo Roshi Kaisha, Ltd.).

(3) Subsequently, a solvent replacement step was performed in which 200 mL of tertiary butyl alcohol ($^t$BuOH, 06104-25, Nacalai Tesque Inc.) was dropped onto the dehydrated nanocellulose aggregate and filtered.

(4) The obtained nanocellulose aggregate in a wet state was subjected to a hot press drying treatment (AYSR-5, Shinto Metal Industries, Ltd.) under conditions of 110° C., 1 MPa, and 15 min, and then peeled off from a PTFE membrane filter to obtain a film.

(5) The manufactured film was cut into a square having one side of 1 cm, to manufacture the device 1. FIG. 8A shows an SEM photograph of the manufactured device 1 in Example 1. FIG. 9 shows a graph showing the result of the pore size distribution of the pores of the manufactured film, measured by mercury intrusion method. FIG. 9A shows a graph showing the distribution for the scale of the pore size of 1 nm to 100 nm, and FIG. 9B shows a graph showing the distribution for the scale of the pore size is of 1 nm to 100 μm. From FIGS. 9A and 9B, it was confirmed that the films manufactured in Example 1 have a nanopore distribution of about 4 nm to 300 nm and the average size is about 60 nm.

Example 2

A film-like device was fabricated from cellulose nanofibers in the same manner as for Example 1, except that the replacement step by tBuOH of the Example 1 was not performed. FIG. 8B shows an SEM photograph of the device manufactured in Example 2. As is apparent from the photograph, the device manufactured in Example 2 did not form nanopores between the cellulose nanofibers. Since there must be nanopores, the size of the nanopore of Example 2 is considered to be 1 nm.

Example 3

A film-like device with micro-sized pores was manufactured from pulp (cellulose fiber) by the following procedure.

(1) 400 mg of conifer bleached kraft pulp was introduced into 200 mL of water to obtain a pulp aqueous dispersion.

(2) The above pulp aqueous dispersion was filtered and dehydrated using a filtration device (KG-90, Advantek Toyo Roshi Kaisha, Ltd.) and an aspiration device (Aspirator AS-01, AS ONE Corporation) and through a stainless-steel mesh filter (SUS304, 300 mesh, Clever Inc.).

(3) Subsequently, a solvent replacement step was performed in which 200 mL of tertiary butyl alcohol ($^t$BuOH, 06104-25, Nacalai Tesque Inc.) was dropped onto the dehydrated pulp aggregate and filtered.

(4) The obtained wet pulp aggregate was subjected to a hot press dry treatment (AYSR-5, Shinto Metal Industries, Ltd.) under conditions of 110° C., 1 MPa and 15 min, and then peeled off from the stainless mesh filter to obtain a film.

(5) The manufactured film was cut into a square having one side of 1 cm, to manufacture the device 3. FIG. 8C shows a photograph of the manufactured device 3 in Example 3. FIG. 9A and FIG. 9B show the pore size distributions measured by the mercury-intrusion method. As is evident from FIGS. 9A and 9B, the pore sizes of the manufactured films were multi-scale of about 7 nm to 100 nm, and about 1 μm to 100 μm.

Example 4

A film-like device was fabricated from pulp (cellulose fiber) in the same manner as for the Example 3, except that the replacement step by $^t$BuOH of Example 3 was not performed. FIG. 8D shows a photograph of the manufactured in Example 4. FIG. 9A and FIG. 9B show the pore size distributions measured by the mercury-intrusion method. As can be seen from FIGS. 9A and 9B, the pore size of the manufactured film was about 1 μm to 100 μm.

Example 5

A device embedded in a flow channel in which nanowires were formed on a substrate was manufactured by the following procedure. (1) First, a channel patterning of a PDMS embedded nanowire device was done on the Si(100) substrates (Advantech Co, Ltd.). A positive resist (OFPR-8600 LB, Tokyo Ohka Kogyo Co. Ltd.) was spin-coated on the Si substrate surface under conditions of 500 rpm (5 sec) and 3000 rpm (120 sec) by a spin coater (MS-A100, Mikasa Corporation), and then the Si substrate surface was heated on a hot plate at 90° C. for 12 min to evaporate the solvent and fix the resist on the substrate. A glass mask was placed on the heated substrate, and the resist was softened by irradiating the substrate with i-line of 600 mJ/cm$^2$ by an exposure machine. Finally, the softened resist was removed by immersing the substrate in a developer (NMD-3, Tokyo Ohka Kogyo Co., Ltd.) for about 10 seconds, and the substrate was taken out of the developer and washed with flowing water. Then, the substrate was heated at 90° C. for 5 min on a hot plate to complete the patterning.

(2) Next, a Cr layer was made, which becomes a seed layer of the nanowire growth on the substrate surface. With the condition of the sputtering device (EIS-200ERT-YN, Elionics Corporation) for preparing the Cr layer was 1.2× 10$^{-2}$ Pa for 14 min, a 135 nm-thick Cr layer was deposited. The substrate was immersed in 2-propanol warmed to 70° C. on a hot plate for 40 min, and then subjected to an ultrasonic treatment for 2 min with an ultrasonic instrument to roughly remove the resist outside the flow path. Thereafter, the substrate was transferred to 2-propanol at 70° C. placed in another container, and after immersion for 10 min, the resist outside the flow path was completely removed by performing an ultrasonic treatment for 1 min Finally, fine Cr particles on the substrate were removed by rinsing in 2-propanol at 70° C. in another container. By these steps, the Cr layer deposition was only in the flow path portion on the substrate. This substrate was heated in an electric furnace at 400° C. for 2 h to oxidize the Cr layer and to complete the seed layer manufacture of the nanowire growth.

(3) To 200 mL of ultrapure water, hexamethylenetetramine (HMTA; 085-00335, Wako Pure Chemical Industries, Ltd.) was dissolved so as to become 15 mM, and it was stirred by a stirrer for 7 min. Thereafter, the solution was further dissolved so that zinc nitrate hexahydrate (12323, Alfa Aesar) became 15 mM, and then stirred for 7 min to obtain a nanowire growth solution. Here, two substrates on which a Cr oxide layer was deposited in the form of a flow path prepared by the above procedure were bonded to a 76 mm×52 mm×0.8 to 1.0 mm slide glass with a carbon tape, immersed in the growth solution, and heated in an airblowing constant-temperature high-temperature apparatus at 95° C. for 3 hours to grow nanowires. Subsequently, the substrate was removed from the beaker and washed away with ultrapure water to remove non-specifically grown nanowires.

(4) The substrate on which the nanowires manufactured in (3) above were grown was stuck on the petri dish. PDMS prepolymer (Silpot 184, Dow Corning Toray Ind., Ltd.) and the curing agent (Silpot 184 CAT, Dow Corning Toray Ind., Ltd.) were poured into the dish at a weight ratio of 10:1 and then mixed under conditions of 2000 rpm, 2 min, 2200 rpm, and 6 min. This was evacuated for 2 h to remove bubbles in the polymer, and then the polymerization proceeded by heating on a hot plate at 80° C. for 2 h to cure the polymer. These operations embedded the nanowires on the Si-substrate into PDMS. PDMS in which these nanowires were embedded was exfoliated from the Si substrate, and PDMS embedded nanowires were stuck on the slide glass. Then, under the same condition as in (3) above, the nanowires embedded in PDMS were grown. After the growth, the embedded nanowires were removed from the beaker, and the non-specifically grown nanowires were removed by washing away with ultrapure water, thereby completing the manufacture of PDMS embedded nanowires.

(5) A negative-type photoresist (SU-8 3025, Nippon Kayaku Co., Ltd.) was applied on a silicon substrate by a spin-coater, covered with a photomask having a shape in which the flow path portion can be exposed, and exposed and developed to manufacture a mold in which the portion forming the flow path becomes convex. Next, the manufactured mold was placed in a petri dish. Next, a PDMS prepolymer and a curing agent similar to those described in (4) above were put in a container at a weight ratio of 10:1, and then mixed at the condition of 2000 rpm for 2 min, and 2200 rpm for 6 min, and it was poured into a petri dish and vacuum-drawn for 2 h to remove bubbles in the polymer. After 2 hours, the polymerization was proceeded by heating on a hot plate at 80° C. for 2 hours to cure the polymer. The cured polymer was cut out, an introduction hole and a collection hole were opened with a punch of 0.32 mm in the flow path, to prepare a cover member. (6) Finally, on the substrate having nanowires manufactured in (4) above, the cover member manufactured in (5) above was placed. Further, a device 5 was manufactured by inserting PEEK tubes into the introduction hole and the collection hole and fixing the tubes with adhesive. FIG. 6E shows an enlarged photograph of the nanowires of the device manufactured in Example 5.

Extraction and Analysis of miRNA
(Extraction/Analysis Example 1)

Using saliva as the sample solution and using devices manufactured in Examples 1 to 4 as the device, the extraction of miRNA from EVs contained in saliva and the analysis were performed by the following procedure.

(1) Preparation of Sample Solution

Saliva was collected from the subjects. In Extraction/Analysis Example 1, saliva is used as it is, but in order to remove impurities in saliva, saliva may be placed in a centrifuge tube if necessary, and impurities may be removed by centrifugation. Note that this centrifugation is just for removing impurities and different from the ultracentrifugation for fractionating and collecting EVs.

(2) Capture of EVs in samples

10 µl of saliva sample was dropped to Examples 1 to 4 and allowing them to stand for about 10 seconds, to capture EVs in the saliva sample in the device. Next, the device was picked with tweezers and immersed in PBS for about 10 seconds to clean RNase and the like.

(3) Extraction of miRNA

Cell lysis buffer M (038-21141, Wako) was used as the disruption solution. 1 ml of disruption solution was put in a centrifuge tube, and then the device in which EVs were captured in (2) above was introduced into a centrifuge tube, and after stirring for about 3 seconds by vortex, the device was allowed to stand for 5 minutes, whereby EVs were directly dissolved from the device in which EVs were captured, and the extraction of miRNA was performed. FIG. 10A shows a photograph when the device of Example 1 was used; (a) a photograph of the centrifuge tube after removing the device 1 from the centrifuge tube after miRNA extraction; and (b) a photograph of the device 1 removed from the centrifuge tube. FIG. 10B shows a photograph when the device of Example 2 was used; (a) a photograph of the centrifugal tube after removing the device 2 from the centrifugal tube after miRNA extraction; and (b) a photograph of the device 2 removed from the centrifugal tube. FIG. 11A shows a photograph when the device of Example 3 is used; (a) a photograph of the centrifuge tube immediately after completion of miRNA extraction step; (b) a photograph of the centrifuge tube after removal of the device 3 from the centrifuge tube after miRNA extraction; and (c) a photograph of the device 3 removed from the centrifuge tube. FIG. 11B shows a photograph when the device of Example 4 was used: (a) a photograph of a centrifuge tube immediately after completion of miRNA extraction step; (b) a photograph of the centrifuge tube after removal of the device from the centrifuge tube after miRNA extraction; and (c) a photograph of the device removed from the centrifuge tube. As shown in FIG. 10A and FIG. 10B, when the devices of Examples 1 and 2 made of cellulose nanofibers were used, no fibers or the like derived from the device were found in the centrifuge tube even after the EVs were disrupted by the disruption solution, and the removed device remained in its original shape. Therefore, after the extraction of miRNA, the miRNA extract could be produced simply by removing the device with tweezers.

On the other hand, as shown in FIG. 11A and FIG. 11B, when the devices made of pulp (cellulose fiber) of Example 3 and Example 4 were used, fibers separated from the device were seen in the centrifuge tube, and the removed device was partially defective. Therefore, in Examples 3 and 4, fibers derived from the device which became an obstacle as impurities at the time of miRNA analysis described later were removed by centrifugation.

(4) miRNA Analysis

Next, the types of miRNA contained in miRNA extract were analyzed using a 3D-Gene (registered trademark) (manufactured by Toray Industries, Ltd.) human miRNA chip by the following procedure. (a) miRNA extract was purified using a SeraMi Exosome RNA purification column kit (System Biosciences Inc.) according to the kit manufacturer's instructions. (b) 15 µl of purified miRNA extract was analyzed using a microarray and a 3D-Gene Human miRNA Oligo chip ver.21 (Toray Industries) for miRNA profiling. 3D-Gene contains 2565 human miRNA probes and can analyze expressions of up to 2565 miRNA types from miRNA extracts. (c) The expression level of each miRNA in the miRNA extract was analyzed by calculating the background-subtracted signal intensity of all miRNA in each microarray, followed by a global normalization.

Figure 10:
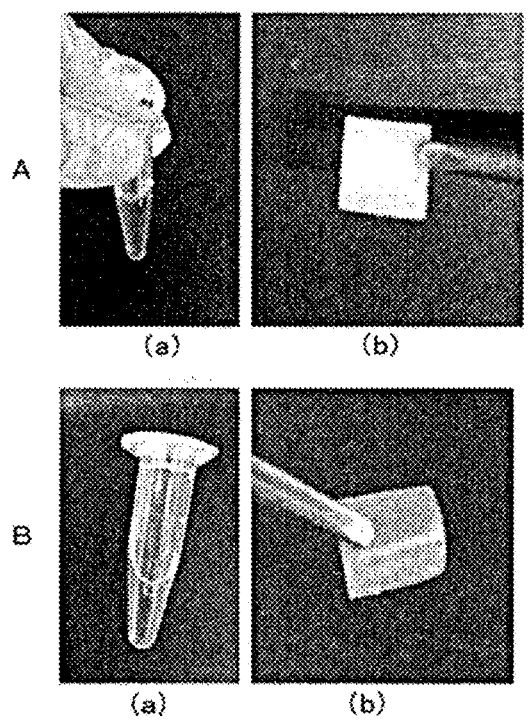

FIG. 12 shows a graph showing the types of miRNA contained in the miRNA extract extracted using the devices of Examples 1 to 4. Note that in each Example an average value of three analysis results is shown. As shown in FIG. 12, it has been confirmed that miRNA can be extracted directly from the EVs captured in the devices even when any of the devices of Examples 1 to 4. Also, as shown in FIG. 10 and FIG. 11, in the devices made from the pulp of Example 3 and Example 4 a portion of the device was defective during the EVs disruption, and fibers separated from the device were seen in the centrifuge tube. Therefore, it became clear that the devices of Example 1 and Example 2 are preferred when the extraction of miRNA from the sample solution is followed by analysis of miRNA.

Note that, in the method of separating EVs by ultracentrifugation of conventional saliva and analyzing miRNA, 27 types of EVs were obtained as described on page 10 in the above Non-Patent Literature 2. In addition, in the above-mentioned Non-Patent Literature 3, as described in FIG. 7, 93 types of miRNA could be analyzed. In addition, in the method described in Non-Patent Literature 3, it is described that 5 ml or even 15 ml of saliva is used, but collecting such a large amount of saliva has a very large burden on the subject (patient). On the other hand, when the devices described in Examples 1 to 4 were used, more than 700 types of miRNA were successfully analyzed using only 10 μl of saliva. In other words, it means that the trace amounts of miRNA as content could also be analyzed.

From the above results, when the device according to the first to fourth embodiments are used, it is possible to simplify the extraction operation procedure of miRNA from the EVs in the saliva sample as compared with the separation method of the EVs using a conventional ultracentrifugation or the like. In addition, since miRNA can be directly extracted from the device that captured the EVs (and EVs in the saliva can be captured by the device at a high rate), the loss during miRNA extracting operation is reduced, and a remarkable effect was confirmed that miRNA analysis can be performed with high accuracy. Therefore, the extraction methods of miRNA disclosed in this application re very useful as a sample preparation method in the analysis method of miRNA contained in a sample solution. In addition, miRNA could be analyzed with high accuracy from saliva, which, as a biological sample solution, is difficult to collect in an invasive manner for a large amount. Thus it is expected that the cancer diagnosis is also carried out by contacting the devices 1 to 4 to tongues at the time of a medical examination or the like.

Extraction and Analysis of miRNA
(Extraction/Analysis Example 2)

Urine was used as the sample solution, and the device prepared in Example 5 was used as the device, and miRNA were extracted and analyzed from EVs contained in the urine by the following procedure.

(1) Sample Preparation 1 mL of commercially available urine (Proteogenex, BioreclamationlVT, μW Biopharma) was dispensed into a 1.5 mL centrifuge tube, and this centrifuge tube was set in a cooled centrifuge, and the impurities were precipitated by centrifugation at 3000×g for 15 min at 4° C. In the following, the supernatant portion excluding this impurity is described as a urine sample.

(2) Capture of EVs in Urine Sample 1 mL of the above urine sample was introduced into the device 5 under the condition of a flow rate of 50 μL/min by a syringe pump, and EVs in the urine sample were captured by the nanowires.

(3) Extraction of miRNA

As disruption solution, the same cell lysis buffer M as in Extraction/Analysis Example 1 was used, and the capture EVs were dissolved by introducing 1 mL of the disruption solution into the device, to prepare a miRNA extract.

(4) miRNA Analysis

Analysis was performed in the same manner as in Extraction/Analysis Example 1.

228 experiments were performed in the same manner, and 1144 types of miRNA could be detected in average, using the devices of Example 5. From the above results, it was confirmed that miRNA could be extracted directly from the EVs captured at the nanowires.

In addition, according to the method of separating EVs by conventional ultracentrifugation and analyzing miRNA, three experiments were carried out by the same procedure. 171, 261, and 352 types of miRNA could be analyzed. In addition, in an experiment using ExoQuick (manufactured by Funacosi Corporation), which is a commercially available EVs concentration kit using a resin based EVs adsorption carrier, 337, 355, and 491 types of miRNA could be analyzed.

From the above results, it was also confirmed that the same remarkable effect as described in Extraction/Analysis Example 1 was obtained even when a biological sample other than saliva and a device for capturing EVs other than a device made of wood fiber were used.

[Influence of Preservation Temperature and Duration of Device That has Captured Extracellular Vesicles on Analysis of Extracellular Vesicles]

Example 6

Using the device (cellulose nanofibers; with nanopores) manufactured in Example 1, experiments were performed by the following procedure.

(1) Preparation of sample solution Saliva was collected from the subjects. The collected saliva was placed in a centrifuge tube and centrifuged for 3000g×15 minutes to remove impurities.

(2) Capture of EVs in sample EVs in saliva sample were captured in the device by dropping 10 μl of saliva sample into the device and allowing it to stand for about 10 seconds.

(3) Drying of device

The device to which the saliva sample was dropped was dried by leaving at room temperature for 10 seconds.

(4) Preservation of device

The device dried in (3) above was preserved at room temperature for 0-6 days, 20 days. The experiment was carried out from October to November, and normal ventilation was carried out in the daytime laboratory. Also, for any number of days it was performed with N=3.

(5) Analysis of extracellular vesicles

The preserved devices were washed by immersion in PBS for 10 seconds, and sRNA concentration (ng/μl) was determined by the following procedure. In Example 5, the influence of preservation on EVs was examined by examining changes in RNA concentration. Since the concentration measurement of miRNA is difficult, the concentration of sRNA was used in Example 5.

(a) For one sample measurement, 199 μL of Qubit (registered trademark) Buffer and 1 μL of Qubit reagent (fluorescent reagent; manufactured by Thermo Fisher Scientific Co., Ltd.) were mixed to prepare 200 μL of solution (Solution A). To measure N samples, [N+2 (for calibration curve)]×200 μL was prepared.

(b) 190 μL of Solution A and 10 μL of a 0 ng/μL sRNA solution (manufactured by Thermo Fisher Scientific Co., Ltd.) were mixed to prepare 200 μL of a mixed solution.

(c) 190 μL of Solution A and 10 μL of 10 ng/μL sRNA solution were mixed to prepare 200 μL of a mixed solution.

(d) The above (b) and (c) were vortexed for 2-3 seconds, respectively, and allowed to stand for 2 minutes.

(e) After carrying out the step of (d), 199 μL of Qubit (registered trademark) Buffer and Qubit reagent (fluorescent reagent; manufactured by Thermo Fisher Scientific Co., Ltd.) were used to measure the fluorescence intensity and the calibration curve was made.

(f) Cell lysis buffer M (038-21141, Wako) was used as the disruption solution. 1 ml of disruption solution was placed in a centrifuge tube, and then the device preserved in (4) above was charged into a centrifuge tube, and the mixture was stirred by vortex for about 3 seconds, followed by standing for 5 minutes to prepare a sample solution in which EVs were dissolved from the device in which EVs were captured. 195 µL of Solution A and 5 µL of the prepared sample were mixed to prepare 200 µL of a mixed solution.

(g) (f) above was vortexed for 2-3 seconds and allowed to stand for 2 minutes.

(h) The concentration of (g) was measured in the same manner as in (e) above, and the concentration was determined on the basis of the calibration made in (e) above.

Example 7

The experiment was conducted in the same manner as in Example 5 except that the preservation temperature was 4° C.

Comparative Example 1

Experiments were performed in the same manner as in Example 5, except that the device (cellulose nanofibers; no nanopores) manufactured in Example 2 was used.

FIG. 13 shows a graph showing the analysis results of Examples 5 and 6 and Comparative Example 1. As shown in the graph, when the device with the nanopores was used (Examples 5 and 6), a remarkable effect on the preservation stability was shown from the second day, compared to when the device without the nanopores was used (Comparative Example 1). In addition, when the device with nanopores was used, there was no particular influence on the analysis accuracy of extracellular vesicles due to the difference in preservation temperature, more specifically, between room temperature (Example 5) and 4° C. (Example 6). When a sample is captured in a device at a remote medical institution, several days to one week are required to transfer the sample to a medical institution with an analysis function and analyze the extracellular vesicles. Therefore, it has been confirmed that among the devices disclosed in the present application, when a device having nanopores in particular is used, the preservation stability is excellent and the transfer is possible in a preservation state at room temperature, so that the convenience of the transfer of the sample is improved.

FIG. 14A is a SEM-photograph before saliva is dropped in Example 5. Further, FIG. 14B is a SEM-photograph after saliva is dropped and dried, in Example 5. As shown in FIG. 14A, a large number of nanopores were formed on the surface of a device made of cellulose nanofibers which was subjected to a substitution step with a medium having a lower surface tension such as tBuOH in Example 1. On the other hand, as shown in FIG. 14B, nanopores were closed on the surfaces of the devices to which saliva was dropped and dried. Since the surface tension of saliva, which is a water-based sample, is larger than that of tBuOH, it is considered that the force for closing the nanopores was exerted in the process of drying the saliva (the arrows in FIG. 14B indicate EVs partially exposed). As shown in FIG. 13, it is considered that the preservation stability increases when the device prepared in Example 1 is used because the EVs are confined between the cellulose nanofiber fibers and the contact with air is reduced.

INDUSTRIAL APPLICABILITY

By using the devices disclosed in the present application, miRNA can be extracted and analyzed from a sample solution simply and with a high accuracy. Therefore, it is useful for cell experiments, etc. in medical institutions, universities, companies, research institutions, etc.

REFERENCE SIGNS LIST 1, 1a-1b . . . device, 2, 2a . . . substrate, 3 . . . nanowire, 4 . . . cover member, 5 . . . catalyst layer, 6 . . . resist, 41 . . . cover member base material, 42 . . . flow path, 43 . . . sample introduction hole, 44 . . . sample collection hole, 45 . . . surface opposite to second surface, 46 . . . non-planar region, 47 . . . second surface

The invention claimed is:

1. A method of preserving extracellular vesicles, the preserving method comprising:
an extracellular vesicle capture comprising bringing a device and a sample solution into contact with each other, to capture an extracellular vesicle in the sample solution in the device;
a drying comprising removing a liquid of the sample solution which impregnated the device; and
a preserving comprising preserving the device which is dried in the drying step and has captured the extracellular vesicle,
wherein, the device comprises a nanostructure body made using cellulose nanofibers.

2. The preserving method according to claim 1, wherein the preserving is carried out at room temperature.

3. The method according to claim 1, wherein the extracellular vesicle is confined in a nanopore in the dried device.

4. The method according to claim 1, wherein the sample solution is a non-invasive biological sample solution.

5. The method according to claim 4, wherein the biological sample solution is saliva.

6. A method of transferring an extracellular vesicle, the transfer method comprising:
an extracellular vesicle capture comprising bringing a device and a sample solution into contact with each other, to capture an extracellular vesicle in the sample solution in the device;
a drying comprising removing a liquid of the sample solution which impregnated the device; and
a transfer comprising transferring the device which is dried in the drying and has captured the extracellular vesicle,
wherein, the device comprises a nanostructure body made using cellulose nanofibers.

7. The transfer method according to claim 6, wherein the transfer is carried out at room temperature.

8. The method according to claim 6, wherein the extracellular vesicle is confined in a nanopore in the dried device.

9. The method according to claim 6, wherein the sample solution is a non-invasive biological sample solution.

10. The method according to claim 9, wherein the biological sample solution is saliva.

11. A method of extracting miRNA from extracellular vesicles, the extraction method comprising:

an extracellular vesicle capture comprising bringing a device and a sample solution into contact with each other, to capture an extracellular vesicle in the sample solution in the device;

a drying comprising removing a liquid of the sample solution which impregnated the device; and a preserving comprising preserving the device which is dried in the drying and has captured the extracellular vesicle, an extracting miRNA from the captured extracellular vesicle, wherein, the device comprises a nanostructure body made using cellulose nanofibers.

12. The method according to claim 11, wherein the extracellular vesicle is confined in a nanopore in the dried device.

13. The method according to claim 11, wherein the sample solution is a non-invasive biological sample solution.

14. The method according to claim 13, wherein the biological sample solution is saliva.

* * * * *